United States Patent [19]

Sebag et al.

[11] Patent Number: 4,587,321

[45] Date of Patent: May 6, 1986

[54] POLYQUATERNARY POLYSILOXANE POLYMERS

[75] Inventors: Henri Sebag; Alexandre Zysman, both of Paris, France

[73] Assignee: L'Oreal, Paris, France

[21] Appl. No.: 718,428

[22] Filed: Apr. 1, 1985

Related U.S. Application Data

[62] Division of Ser. No. 550,418, Nov. 7, 1983, Pat. No. 4,533,714.

[30] Foreign Application Priority Data

Nov. 10, 1982 [LU] Luxembourg .......................... 84463

[51] Int. Cl.[4] ............................................. C08G 77/04
[52] U.S. Cl. ...................................... 528/27; 8/405; 8/406; 424/61; 424/70; 524/588; 528/28; 528/33; 528/38; 556/413; 556/450; 556/462
[58] Field of Search ............... 424/70, 61; 8/405, 406; 528/27, 28, 33, 38; 556/413, 450, 462; 524/588

[56] References Cited

U.S. PATENT DOCUMENTS

| | | | |
|---|---|---|---|
| 4,275,184 | 6/1981 | Bargain et al. | 528/26 |
| 4,293,397 | 10/1981 | Sato et al. | 528/26 |
| 4,381,919 | 5/1985 | Jacquet et al. | 8/406 |
| 4,425,364 | 1/1984 | Vanlerberghe et al. | 424/70 |
| 4,496,705 | 1/1985 | Florence et al. | 556/424 |

Primary Examiner—Melvyn I. Marquis
Attorney, Agent, or Firm—Cushman, Darby & Cushman

[57] ABSTRACT

Quaternary siloxane polymers of the formula:

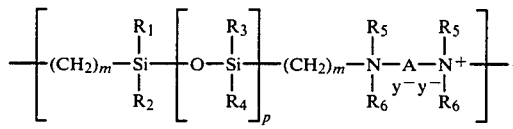

in which A denotes an $\alpha,\beta$-bis-alkylpolysiloxane or a $C_{1-6}$ hydrocarbon chain which can contain OH groups and can be interrupted by one or more oxygen atoms and/or aromatic rings; $R_1$, $R_2$, $R_3$ and $R_4$, which are identical or different, denote a $C_1$-$C_6$ alkyl or phenyl; $R_5$=methyl, ethyl or —$CH_2$—; $R_6$=$C_1$-$C_{18}$ alkyl or —$CH_2$—; if $R_5$ and/or $R_6$ denote —$CH_2$—, they form a methylpiperazinium radical or ethylpiperazinium radical, a diethylenediamine radical or a heterocycle with —N—A—N—; Y denotes one of the anions $Cl^-$, $Br^-$, $CH_3SO_3^-$,

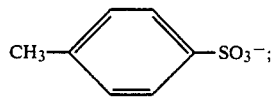

$m=1-6$; and $p=1-50$ are disclosed for use, in particular, for treating the hair, nails and skin. They are resistant to several rinses on these substrates.

22 Claims, No Drawings

POLYQUATERNARY POLYSILOXANE POLYMERS

This is a division, of application Ser. No. 550,418, filed Nov. 7, 1983, now U.S. Pat. No. 4,533,714.

This invention relates to polyquaternary polysiloxane polymers, processes for their preparation and compositions in which they are present, and, in particular, to the use of these compositions in the cosmetics industry, especially for hair care and hair treatments.

It is known to incorporate quaternary polymers into hair-conditioning compositions in order to improve the comb-out and the cosmetic condition of the hair. However, the cosmetic compositions for the hair which contain known quaternary polymers still have disadvantages.

It has been discovered that the polymers of the present invention, when applied to the hair in the form of an aqueous composition, improve the comb-out of the hair, in particular compared with poly-(quaternary ammonium) polymers with a hydrocarbon chain, and leave the hair with little static electricity (which facilitates styling) and in good cosmetic condition.

The novelty of the polymers of this invention derives essentially from the position of the ammonium groups and the distribution of the siloxane groups which they contain.

The present invention provides polyquaternary polysiloxane polymers essentially consisting of repeat units of the general formula:

$$\left[-(CH_2)_{\overline{m}}\underset{\underset{R_2}{|}}{\overset{\overset{R_1}{|}}{Si}}-\left[O-\underset{\underset{R_4}{|}}{\overset{\overset{R_3}{|}}{Si}}\right]_p-(CH_2)_{\overline{m}}\underset{\underset{R_6}{|}\ Y^{\ominus}}{\overset{\overset{R_5}{|}}{N^{\oplus}}}-A-\underset{\underset{R_6}{|}\ Y^{\ominus}}{\overset{\overset{R_5}{|}}{N^{\oplus}}}-\right] \quad (I)$$

in which:

A denotes a divalent α,ω-bis-(alkyl)-polysiloxane group or a linear or branched, saturated or unsaturated hydrocarbon chain containing up to 6 consecutive carbon atoms, which can contain one or more hydroxyl groups and can be interrupted by one or more oxygen atoms and/or one or more aromatic rings; by way of example, A can represent the following groups:

$$+(CH_2)_m-\underset{\underset{R_2}{|}}{\overset{\overset{R_1}{|}}{Si}}-\left[O-\underset{\underset{R_4}{|}}{\overset{\overset{R_3}{|}}{Si}}\right]_p-(CH_2)_m-$$

$R_1$, $R_2$, $R_3$, $R_4$, m and p having the meanings below,

—$(CH_2)$—$_n$, in which n=2 to 6
—$CH_2$-CH=CH-$CH_2$—
—$CH_2$-C≡C-$CH_2$—

$$-\underset{\underset{CH_3}{|}}{CH}-(CH_2)_2-$$

—$CH_2$-CHOH-$CH_2$—
—$CH_2$-CHOH-$CH_2$-O-$CH_2$-CHOH-$CH_2$—
—$CH_2$-$CH_2$-O]$_x$$CH_2$-$CH_2$—, in which x=1 to 15

$$-CH_2-\underset{}{\underset{}{\bigcirc}}-CH_2- \text{ and } -CH_2-CHOH-CH_2-O-\underset{}{\underset{}{\bigcirc}}-\underset{\underset{CH_3}{|}}{\overset{\overset{CH_3}{|}}{C}}-\underset{}{\underset{}{\bigcirc}}-O-CH_2-CHOH-CH_2-$$

$R_1$, $R_2$, $R_3$ and $R_4$, which are identical or different, denote a $C_1$-$C_6$ alkyl radical or the phenyl radical; the methyl radical radical is the preferred alkyl radical;

$R_5$ denotes the methyl, ethyl or hydroxyethyl radical or, alternatively, under the conditions specified below, the divalent radical —$CH_2$—;

$R_6$ denotes a $C_{1-18}$ alkyl radical; $R_6$ can also denote the divalent radical —$CH_2$— (in this case, A denotes —$CH_2$—$CH_2$—) and can form:
(i) a divalent piperazino group with the two nitrogen atoms and A, or
(ii) the divalent triethylenediamino radical of the formula:

$$-N\underset{\underset{CH_2-CH_2}{\diagdown}}{\overset{\overset{CH_2-CH_2}{\diagup}}{\underset{-CH_2-CH_2-}{\diagup\diagdown}}}N-$$

with the two nitrogen atoms, A and $R_5$ (which in this case denotes —$CH_2$—);

$R_6$ and $R_5$ can also be joined to one another and can denote a heterocycle, such as piperidino, morpholino or pyrrolidino, with the nitrogen atom to which they are attached;

$Y^{\ominus}$ denotes one of the anions $Cl^{\ominus}$ or $Br^{\ominus}$ ($Cl^{\ominus}$ and $Br^{\ominus}$ can also be denoted by $X^{\ominus}$) or the anion $CH_3SO_3^{\ominus}$ or $$CH_3-\underset{}{\underset{}{\bigcirc}}-SO_3^{\ominus};$$

m denotes an integer from 1 to 6 and preferably from 1 to 4; and p denotes an integer or decimal number from 1 to 50 and preferably 1 to 10; p can represent an integer, or a statistical average value in the case of a polymer mixture.

The polymers of the formula (I) according to the invention can be prepared by known processes, for example by reaction of the compound of the formula (III)

$$Y-(CH_2)_m-\underset{\underset{R_2}{|}}{\overset{\overset{R_1}{|}}{Si}}-\left[O-\underset{\underset{R_4}{|}}{\overset{\overset{R_3}{|}}{Si}}\right]_p-(CH_2)_m-Y \quad (III)$$

with a bis-tertiary diamine of the formula (IV)

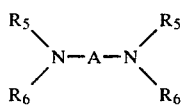

In the compounds of the formulae (III) and (IV), $R_1$, $R_2$, $R_3$, $R_4$, $R_5$, $R_6$, Y, A, m and p have the meanings indicated above.

The polysiloxanes of the formula (III)

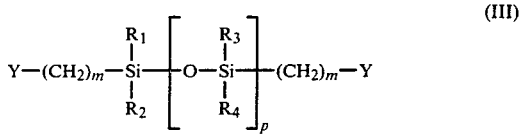

can be prepared by the known reactions, for example, when m=3:

(1) by reaction of a dialkylchlorosilane with an allyl halide, in the presence of platinum or chloroplatinic acid used as a catalyst, to give a halogenopropyldialkylchlorosilane, which, on hydrolysis and condensation, gives the bis-(halogenopropyl)-1,1,3,3-tetraalkyldisiloxane.

The dialkylchlorosilane can be replaced by a diphenylchlorosilane, by an alkyl-phenylchlorosilane or by a mixture of these compounds.

(2) by reaction of a dialkylchlorosilane, a diphenylchlorosilane or an alkyl-phenylchlorosilane with allyl acetate, in the presence of platinum or chloroplatinic acid, to give the acetoxypropyl-dialkylchlorosilane, which, on hydrolysis and condensation, leads to the 1,3bis-(3-hydroxypropyl)-1,1,3,3-tetraalkyldisiloxane.

Halogenation of this compound with a halogenating agent such as phosphorus tribromide, $PBr_3$, or thionyl chloride, $SOCl_2$, leads to the 1,3-bis-(halogenopropyl)1,1,3,3-tetramethyldisiloxane.

If a mesyl or tosyl halide is used, a compound of the formula (III) is obtained in which Y denotes $CH_3SO_3$ or $CH_3-C_6H_4-SO_3$ respectively.

The 1,3-bis-(halogenopropyl)-1,1,3,3-tetraalkyldisiloxane can also be obtained directly by reaction of the 1,1,3,3-tetraalkyldisiloxane with the allyl halide. This reaction also produces a second compound, namely 1,1,3,3-tetraalkyl-3-halogenopropyl-1-halogenodisiloxane, which, on hydrolysis, makes it possible to obtain the 1,7-bis-(halogenopropyl)-octaalkyltetrasiloxane of the formula:

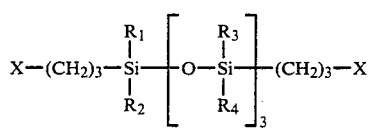

(3) by reaction of a compound (a), which can be a dialkyldichlorosilane, a diphenyldichlorosilane or an alkyl-phenyldichlorosilane, or a mixture of these compounds, with a compound (b) chosen from:
(b1) a dialkyl-halogenoalkyl-halogenosilane,
(b2) a dialkyl-acetoxyalkyl-halogenosilane,
(b3) a dialkyl-acetoxyalkyl-acetoxysilane,
(b4) a tetraalkyl-acetoxyalkyl-acetoxydisiloxane,
(b5) a dialkyl-halogenoalkyl-methoxysilane or dialkyl-halogenoalkyl-ethoxysilane,
(b6) a dialkyl-acetoxyalkyl-methoxysilane or dialkyl-acetoxyalkyl-ethoxysilane,
(b7) a tetraalkyl-halogenoalkyl-methoxydisiloxane or tetraalkyl-halogenoalkyl-ethoxydisiloxane, and
(b8) a tetraalkyl-acetoxyalkyl-methoxydisiloxane or tetraalkyl-acetoxyalkyl-ethoxydisiloxane, this reaction being followed by saponification and then by halogenation of the resulting compound with a halogenating agent such as phosphorus tribromide, $PBr_3$, thionyl chloride, $SOCl_2$, or a methyl or tosyl halide.

These reactions can be carried out with or without a solvent, if appropriate in the presence of electrolytes, at a temperature of, say, 0° to 120° C. As solvents which can be used, there may be mentioned water, lower alcohols having from 1 to 4 carbon atoms, cyclic ethers such as tetrahydrofuran or dioxane, aliphatic or aromatic hydrocarbons, or mixtures of these solvents.

The bis-tertiary diamines (IV) which can be used according to the invention are preferably symmetrical amines such as N,N'-tetramethylethylenediamine, N,N'-tetramethylpropylenediamine, N,N'-tetramethylbutylenediamine, N,N'-tetramethylhexamethylenediamine, N,N'-dimethyl-N,N'-dialkyl($C_1$-$C_{18}$)alkylene($C_2$-$C_6$)-diamines, 1,4-tetramethyldiaminobut-2-ene, 1,4-tetramethyldiaminobut-2-yne, dihydroxyethylpiperazine, 1,3-bis(methyl-alkyl($C_{1-18}$)amino)-propan-2-ols, 1,3-bis-(methylhydroxyethylamino or ethylhydroxyethylamino)-propan-2-ol and 1,3-bis-(morpholino)-propan-2-ol.

The compounds of the formula (I) can also be obtained, in a second process, by reaction of a bis-tertiary diamine of the formula (V):

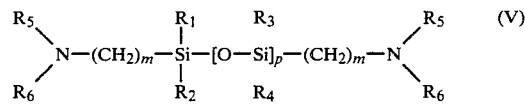

with a bis-halogenated derivative or a bis-mesylated or bis-tosylated derivative of the formula (VI):

A, $R_1$, $R_2$, $R_3$, $R_4$, $R_5$, $R_6$, Y, m and p having the meanings indicated above.

The diamino compounds of the formula (V) can be obtained by reaction of the difunctional derivatives (III) with the corresponding secondary amines

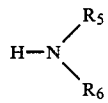

or alternatively, when m=3, by reaction of the dihydropolysiloxane derivative with the substituted allylamine.

Examples which may be mentioned of the difunctional derivatives (VI) are the compounds (III), alkyl or xylyl dihalides, the bis-chlorohydrin of glycerol or diglycerol, the bis-3-chloro-2-hydroxypropyl ether of bisphenol A, and α,ω-halogenated, α,ω-mesylated or α,ω-tosylated derivatives of ethylene or polyethylene glycol.

The polyquaternary polysiloxane polymers of the formula (I) according to the invention can be obtained by heating the compounds of the formulae (III) and (IV) or the compounds of the formulae (V) and (VI) in water or in various solvents such as alcohols having from 2 to 4 carbon atoms, glycols, glycol ethers, aliphatic or aromatic hydrocarbons, ketones such as methyl ethyl ketone or methyl isobutyl ketone, or mixtures thereof, at temperatures of, say, 80° to 150° C., if appropriate under pressure.

The polyquaternary polysiloxane polymers obtained after polymerisation usually have a molecular weight of 500 to 50,000.

The polymers according to the invention are soluble or dispersible in water or in an aqueous-alcoholic medium and are preferably used at a concentration of 0.1 to 10% and more advantageously of 0.2 to 5%, by weight, by themselves or in combination with one or more cosmetic adjuvants, in cosmetic compositions for treating the hair, nails or skin.

In aqueous solution, these polymers have a good affinity for keratin fibres, on which they form a rinseresistant deposit.

If the cosmetic compositions containing the polymers according to the invention are applied to the hair, they make the hair easier to comb out and shape, while at the same time imparting softness and shine and leaving the hair with little static electricity, which also facilitates styling. Furthermore, the polymers according to the invention are rather mild towards the skin or the mucous membrane of the eye.

This invention also provides cosmetic compositions containing at least one polyquaternary polysiloxane polymer for treating the hair, nails and skin, and more particularly for hair care.

The cosmetic compositions can be applied to the hair as pretreatments, facilitating the subsequent fixing of anionic active substances, for example, or as post-treatments, such as lotions, rinse-off lotions or styling gels, or they can constitute the main treatment in the form of a shampoo, setting lotion or dye.

The cosmetic compositions according to the invention can be aqueous, aqueous-alcoholic or solvent-based and, if appropriate, can contain oils; they can be presented in the form of solutions, lotions, creams, dispersions, gels or aerosols, for example.

In addition to the polymer essentially consisting of units corresponding to the formula (I), the cosmetic compositions according to the invention can contain any component used in cosmetic compositions, in particular anionic, cationic, amphoteric, zwitterionic or non-ionic surface-active agents, foam synergistic agents, foam stabilisers, opacifiers, sequestering agents, thickeners, emilsifying agents, softeners, preservatives, protein derivatives, natural substances, colorants, perfumes and anionic, cationic amphoteric and non-ionic polymers.

This invention thus provides cosmetic compositions for treating the hair which contain at least one polyquaternary polysiloxane polymer of the formula (I) and at least one anionic polymer, if appropriate in the presence of another cationic compound; these compositions can contain other adjuvants normally used in cosmetics.

When the compositions according to the invention constitute shampoos, they are generally in the form of aqueous solutions and comprise, in addition to the polymer consisting of units of the formula (I), at least one anionic, cationic, non-ionic or amphoteric detergent.

In these shampoos, the concentration of detergent is generally from 1 to 50% and preferably from 1 to 30%, by weight, relative to the total weight of the composition, and the pH is generally from 3 to 9.

The compositions in the form of shampoos also generally contain various adjuvants, in particular perfumes, preservatives, thickeners, foam stabilisers and colorants. The proportion of these adjuvants, expressed in % by weight of the total weight of the composition, is generally 0.5 to 10% for the foam stabilisers, 0.1 to 5% for the thickeners, and 0.01 to 3% for each of the perfumes, colorants and preservatives.

When the compositions according to the invention constitute lotions, they are usually aqueous or aqueous-alcoholic solutions containing a lower alkanol having from 1 to 4 carbon atoms, and preferably ethanol or isopropanol in an amount of 5 to 70%, and, if appropriate, other cosmetic polymers and/or surface-active agents.

The compositions according to the invention can also constitute treatment creams in the form of an emulsion containing the polymer consisting of units of the formula (I). These creams can also contain colorants, in particular oxidation dyestuffs and/or direct dyestuffs, and can constitute dyeing creams or colouring creams.

The compositions according to the invention can also be used in a reducing or oxidising solution for perming, in order to curl the hair.

The cosmetic compositions according to the invention generally have a pH of 3 to 12 and preferably 3.5 to 8.5.

If the compositions are packaged in the form of aerosols, they contain a propellent gas.

This invention also provides a process for treating the hair, nails or skin, essentially characterised in that a composition as defined above is applied to the hair, nails or skin in a sufficient amount to condition the hair, nails or skin.

This invention is further illustrated by the following Examples.

PREPARATION EXAMPLES

EXAMPLE 1

Preparation of a mixture of compounds of the formula (I) in which $R_1$, $R_2$, $R_3$, $R_4$, $R_5$ and $R_6$ denote $CH_3$, $m=3$, $p=1$, $Y=Br$, $A=(CH_2)_3$.

182.5 g (1.93 mol) of dimethylchlorosilane and 1.4 g of 5% strength platinum-on-charcoal are introduced into a one litre reactor fitted with a stirrer, a thermometer and a reflux condenser.

242 g (2.42 mol) of allyl acetate are added to this dispersion over a period of 10 minutes, with stirring, and the reaction mixture is then heated for 20 hours under reflux. The catalyst is removed by filtration and the mixture is then topped under a reduced pressure of 50 mm Hg (6.66 kPa).

233 g of dimethyl-acetoxypropylchlorosilane are then distilled under a pressure of 0.1 mm Hg (13.33 Pa) and at a temperature of 53°–55° C.

194.5 g of the product thus obtained are dissolved in one litre of 96° strength ethanol. The solution is cooled in an ice bath and 200 g of a 40% strength aqueous solution of NaOH are added over a period of 20 minutes. The reaction mixture is then heated under reflux for 1 hour. The inorganic salts formed are removed by filtration.

After partial concentration, extraction is carried out twice with 250 ml of chloroform and the extracts are then washed with twice 100 ml of water. The organic phase is dried over anhydrous sodium sulphate and the solvent is removed by evaporation.

This gives 116 g of 1,3-bis-(3-hydroxypropyl)-1,1,3,3-tetramethyldisiloxane: compound A.

200 g (0.7 mol) of $PBr_3$ and 65 ml of dichloroethane are introduced into a one litre reactor and the mixture is cooled in an ice bath. A solution of 200 g (0.8 mol) of the previously obtained compound A in 200 ml of methylene chloride is then added over a period of 15 minutes.

The mixture is stirred for a further one hour in an ice bath, then heated for one hour at 50° C. and then left to stand overnight at ambient temperature.

The solution is subsequently washed with 250 ml of water and then twice with 250 ml of a saturated solution of sodium bicarbonate. The organic phase is dried over anhydrous sodium sulphate and the solvent is removed by evaporation.

Distillation at 102° C. under a pressure of 0.01 mm Hg (1.33 Pa) gives 125 g of 1,3-bis-(bromopropyl)-1,1,3,3-tetramethyldisiloxane (compound $III_1$).

32.7 g (0.25 mol) of N,N'-tetramethyl-1,3-propylenediamine and 37.5 g of water are mixed in a 250 cc reactor. This solution is heated to the reflux temperature and 94 g (0.25 mol) of the compound $III_1$ described above are added over a period of 30 minutes. The reaction medium is thus heated for 13 hours.

This gives a resin which, in the anhydrous state, is almost colourless and soft. It is soluble in water. Its intrinsic viscosity, measured in water at 25° C., is 0.044 dl/g.

EXAMPLE 2

Preparation of a mixture of compounds of the general formula (I) in which $R_1$, $R_2$, $R_3$, $R_4$, $R_5$ and $R_6$ denote $CH_3$, m=3, p=3, Y=Cl, A=$(CH_2)_3$.

93.7 g (0.7 mol) of 1,1,3,3-tetramethyldisiloxane, 160 g (2.1 mol) of freshly distilled allyl chloride and 0.47 g of a 5% strength platinum-on-charcoal catalyst are introduced into a one litre autoclave.

The mixture is heated for 12 hours at 120° C. The catalyst is removed by filtration and the excess allyl chloride is evaporated off under reduced pressure. The residue is then distilled under 9 mm Hg (1,200 Pa).

47.3 g of 1-chloro-3-chloropropyl-1,1,3,3-tetramethyldisiloxane are thus collected at 80°–82° C.

46.3 g of the above compound are run into 100 ml of a saturated solution of sodium chloride over a period of 5 minutes. The mixture is stirred for 40 minutes at 45° C. and then for 40 minutes at ambient temperature and a further 15 minutes at 45° C. The sodium chloride is filtered off and the filtrate is extracted with ether.

After the ether phase has been dried over anhydrous sodium sulphate and the solvent removed by evaporation, the residue is distilled under a pressure of 0.01 mm Hg (1.33 Pa). 21 g of 1,7-bis-(chloropropyl)-1,1,3,3,5,5,7,7-octamethyltetrasiloxane are collected at 113°–116° C.

15.8 g of the difunctional compound prepared in this way (0.036 mol) are solubilised with 4.75 g (0.036 mol) of N,N'-tetramethyl-1,3-propylenediamine in 40 ml of dimethylformamide. The mixture is heated for 20 hours at 125° C. and the polymer is then precipitated in 100 ml of ether.

A soft water-soluble resin having a chloride content of 3.87 meq/g is thus isolated.

EXAMPLE 3

Preparation of a mixture of compounds of the general formula I in which $R_1$, $R_2$, $R_3$, $R_4$, $R_5$ and $R_6$ denote $CH_3$, m=1, p=1, Y=Br, A=$(CH_2)_3$.

1,3-Bis-(bromomethyl)-1,1,3,3-tetramethyldisiloxane is prepared by brominating trimethylchlorosilane with phosphorus tribromide, the resulting compound undergoing condensation on hydrolysis with water.

23.6 g (0.074 mol) of the compound prepared in this way are solubilised with 9.6 g (0.074 mol) of N,N'-tetramethylpropylenediamine in 100 ml of methyl isobutyl ketone. The mixture is heated under reflux for 10 hours. The precipitated polymer is washed with ether and dried.

25.7 g of a clear, very hygroscopic, water-soluble resin are isolated. Its absolute viscosity, at a concentration of 5% in water at 25° C., is 0.96 cps.

EXAMPLE 4

Preparation of a mixture of compounds of the general formula (I) in which $R_1$, $R_2$, $R_3$, $R_4$, $R_5$ and $R_6$ denote $CH_3$, m=3, p=1, A=$(CH_2)_4$, Y=Br.

42.5 g (0.5 mol) of dimethylallylamine and 33.5 g (0.25 mol) of tetramethyldisiloxane are mixed, together with 0.34 g of 5% strength platinum-on-charcoal, in a 250 ml autoclave. The mixture is heated for 5 hours at 120° C. After the catalyst has been filtered off, the volatile compounds are removed by distillation under 50 mm Hg (6.66 kPa). The residue is subjected to distillation under 0.01 mm Hg (1.33 Pa) and 40 g of 1,3-bis(3-dimethylaminopropyl)-tetramethyldisiloxane are isolated at 80°–82° C.

10 g (0.033 mol) of 1,3-bis-(3-dimethylaminopropyl)-tetramethyldisiloxane and 4 ml of water are introduced into a reactor fitted with a stirrer, a thermometer and a reflux condenser. 6.97 g of 1,4-dibromobutane are added rapidly to this solution and the mixture is then heated at 90°–95° C. for 1 hour 45 minutes. This gives a solution of polymer having a bromide content of 3.1 meq/g.

EXAMPLE 5

Preparation of a mixture of compounds of the formula (I) in which $R_1$, $R_2$, $R_3$, $R_4$ and $R_5$ denote $CH_3$, $R_6$ denotes $C_{12}H_{25}$, Y=Br, A=$(CH_2)_6$, p=6, m=3.

A mixture of 129 g (1 mol) of dimethyldichlorosilane and 77.9 g (0.4 mol) of dimethyl-acetoxypropylchlorosilane is added, at between 20° and 25° C., to 500 ml of water saturated with sodium chloride. The mixture is stirred for 4 hours at this temperature. The sodium chloride is removed by filtration and then washed with twice 50 ml of methylene chloride. The filtrate is decanted and the aqueous phase is washed with twice 150 ml of methylene chloride. The organic phases are combined and then washed with 100 ml of a saturated solution of sodium bicarbonate. The organic phase is dried over anhydrous sodium sulphate.

After the solvent has been removed, 128.3 g of a colourless oil are collected, that is to say a yield of 96%.

This oil is dissolved in 700 ml of ethanol. 140 g (1.4 mol) of a 40% strength aqueous solution of NaOH are added to this solution, at between 20° and 25° C., and the mixture is then stirred for 1 hour at this temperature. 700 ml of water are then added and the greater part of the ethanol is removed by evaporation in vacuo. The medium is neutralised by adding 230 ml of 6 N HCl. The medium is extracted with 3 times 200 ml of chloroform. The organic phase is washed with 100 ml of water and dried over anhydrous sodium sulphate.

After evaporation to dryness, 100.4 g of a colourless oil are isolated, that is to say a yield of 90.3%.

All the above oil is dissolved in 60 ml of methylene chloride.

A solution of 27 g of $PBr_3$ in 140 ml of methylene chloride is added to this solution over a period of 1 hour 30 minutes at 5° C. Stirring is continued for 1 hour at ambient temperature and the mixture is then heated at the reflux temperature of the solvent for 3 hours.

The organic phase is washed with 100 ml of a saturated solution of sodium bicarbonate and then with three times 100 ml of water.

It is dried over sodium sulphate and the solvent is then removed by distillation under a pressure of 800 Pa. 81 g of a very slightly coloured oil having a bromine content of 2.45 meq/g are thus collected (compound A).

A solution of 13.2 g (0.016 mol) of the compound A in 15 g of methyl CELLOSOLVE is added to a solution of 7.7 g (0.016 mol) of 1,6-bis-(methyllaurylamino)-hexane in 5 g of methyl CELLOSOLVE.

The mixture is heated for 6 hours at 105° C. and the solvent is then removed under reduced pressure (800 Pa).

20.1 g of a viscous oil soluble in 95° strength ethanol having a bromide content of 1.30 meq/g are collected.

EXAMPLE 6

Preparation of a mixture of the compound of the formula (I) in which $R_1$, $R_2$, $R_3$, $R_4$ and $R_5$ denote $CH_3$, $R_6 = C_8H_{17}$, $Y = Br$, $A = CH_2\text{-}CHOH\text{-}CH_2\text{—}$, $p = 6$, $m = 3$.

A solution of 13.2 g (0.016 mol) of the compound A, prepared according to Example 5, in 15 g of methyl CELLOSOLVE (ethylene glycol monomethyl ether) is added to a solution of 5.5 g (0.016 mol) of 1,3-bis-(methyloctylamino)-propan-2-ol in 5 g of methyl CELLOSOLVE.

The mixture is heated for 10 hours at 105° C. The solvent is removed by distillation under a reduced pressure of 800 Pa.

17.3 g of a very thick oil soluble in 95° strength ethanol and having a bromide content of 1.35 meq/g are thus isolated.

EXAMPLE 7

Preparation of a mixture of compounds of the formula (I) in which $R_1$, $R_2$, $R_3$ and $R_4$ denote $CH_3$, the unit formed by $R_5$, $R_6$, A and the two nitrogen atoms denotes the triethylenediamino radical of the formula:

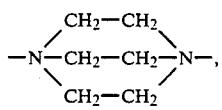

$Y = Br$, $p = 6$, $m = 3$.

A solution of 13.2 g (0.016 mol) of the compound A, prepared according to Example 5, in 15 g of methyl CELLOSOLVE is added to a solution of 1.80 g (0.016 mol) of 2,2,2-diazabicyclooctane in 5 g of methylcellosolve. The mixture is heated for 6 hours at 105° C. The solvent is removed by distillation under 800 Pa. 13.1 g of a thick translucent paste soluble in 95° strength ethanol and having a bromide content of 2.08 meq/g are isolated.

EXAMPLE 8

Preparation of a mixture of compounds of the formula (I) in which $R_1$, $R_2$, $R_3$, $R_4$ and $R_5$ denote $CH_3$, $R_6$ and A form a piperazine ring with the two nitrogen atoms, $Y = Br$, $p = 6$, $m = 3$.

A solution of 13.2 g (0.016 mol) of the compound A, prepared according to Example 5, in 15 g of methyl CELLOSOLVE is added to a solution of 1.82 g (0.016 mol) of N,N'-dimethylpiperazine in 5 g of methyl CELLOSOLVE. The reaction mixture is heated for 15 hours at 105° C. The solvent is evaporated off under a reduced pressure of 800 Pa. 14.5 g of a thick paste soluble in 95° strength alcohol and having a bromide content of 1.78 meq/g are isolated.

APPLICATION EXAMPLES

EXAMPLE A1

| The following shampoo is prepared: | |
|---|---|
| Compound prepared according to Example 1 | 1 g A.I.[(1)] |
| Glucoside alkyl ether containing 30% of active ingredient, sold under the name "TRITON CG 110" by SEPPIC | 18 g |
| Compound of the formula $CH_3(CH_2)_{11}CH_2(OCH_2CH_2)_6OCH_2\text{—}COOH$ sold under the name "Sandopan M acid" by SANDOZ | 3 g |
| NaOH q.s. pH 7.5 | |
| Perfume, colorant, preservative, q.s. | |
| Water q.s. (quantity sufficient for) | 100 g |
| [(1)]A.I = active ingredient. | |

EXAMPLE A2

| The following after-shampoo is prepared: | |
|---|---|
| Compound prepared according to Example 3 | 0.5 g A.I. |
| Mixture of cetyl-stearyl alcohol and cetyl-stearyl alcohol oxyethyleneated with 15 mol of ethylene oxide per mol of alcohol, sold under the name "SINNOWAX A O" by HENKEL | 2 g |
| Cetyl alcohol | 4 g |
| Hydroxymethylcellulose sold under the name "CELLOSIZE QP 4400 H" by UNION CARBIDE | 5 g |
| HCl q.s. pH 7 | |
| Perfume, preservative, colorant q.s. | |
| Water q.s. | 100 g |

EXAMPLE A3

| A rinse-off lotion having the following composition is prepared: | |
|---|---|
| Compound prepared according to Example 1 | 1 g A.I. |
| Distearyldimethylammonium chloride | 1 g |
| Cationic polymer containing units | 0.3 g |

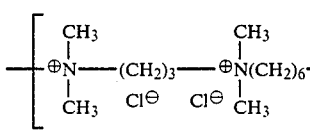

prepared according to French Patent 2,270,846
NaOH q.s. pH 7.3
Perfume, colorant, preservative q.s.

EXAMPLE A4

| The non-ionic shampoo having the following composition is prepared: | |
|---|---|
| Compound of Example 5 | 0.8 g |
| Polyglycerol hydroxyalkyl ether of the formula: R—CHOH CH$_2$—[O—CH$_2$—CHOH—CH$_2$—O]$_{3.5}$H R representing a mixture of alkyl radicals having 9 to 12 carbon atoms | 7 g |
| Diethanolamides of copra fatty acids | 3 g |
| Water q.s. | 100 g |
| pH adjusted to 7.3 | |

EXAMPLE A5

| The following setting lotion is prepared: | |
|---|---|
| Compound of Example 6 | 0.5 g |
| Vinylpyrrolidone/vinyl acetate copolymer (60/40) | 2 g |
| 95° strength ethanol | 15 g |
| Water q.s. | 100 g |
| pH adjusted to 7.4 | |

EXAMPLE A6

| The following after-shampoo is prepared: | |
|---|---|
| Compound of Example 7 | 0.5 g |
| Compound of Example 8 | 0.2 g |
| Mixture of cetyl-stearyl alcohol and cetyl-stearyl alcohol oxyethyleneated with 15 mol of ethylene oxide, sold under the name "SINNOWAX AO" by HENKEL | 2 g |
| Cetyl alcohol | 4 g |
| Hydroxymethylcellulose sold under the name "Cellosize QP 4400H" by Union Carbide | 5 g |
| Water q.s. | 100 g |
| pH adjusted to 7 | |

EXAMPLE A7

| The following rinse-off lotion is prepared: | |
|---|---|
| Compound of Example 8 | 1.2 g |
| Dimethyldistearylammonium chloride | 0.8 g |
| Quaternary polyvinylpyrrolidone copolymer having a molecular weight of 1 million, sold under the name Gafquat 755 by General Aniline | 1 g |
| 95° strength ethanol | 20 g |
| Water q.s. | 100 g |
| pH adjusted to 7.2 | |

We claim:

1. A composition for treating the hair, nails or skin comprising in a diluent or carrier suitable for application to said hair, nails or skin an effective amount of at least one polyquaternary polysiloxane polymer having recurring units of the formula:

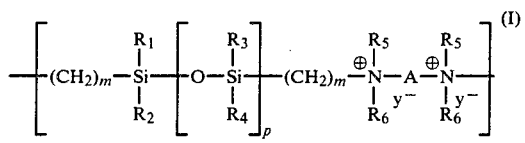

wherein

A represents a divalent α,ω-bis-(alkyl)-polysiloxane group or a linear or branched, saturated or unsaturated hydrocarbon chain containing up to 6 consecutive carbon atoms, optionally substituted by one or more hydroxyl groups and optionally substituted by one or more chain oxygen atoms and/or aromatic rings;

$R_1$, $R_2$, $R_3$ and $R_4$ each independently represent a $C_1$–$C_6$ alkyl radical or a phenyl radical;

$R_5$ represents methyl, ethyl or hydroxyethyl;

$R_6$ represents a $C_1$–$C_{18}$ alkyl radical or two adjacent $R_6$ radicals together with the nitrogen atom to which they are attached and the A radical therebetween form a divalent piperazino radical;

or two adjacent $R_5$ radicals together with the two adjacent $R_6$ radicals attached to the same nitrogen atoms, the said nitrogen atoms and the A radical therebetween form a triethylenediamino radical, or $R_5$ and $R_6$ together represent a heterocycle with the nitrogen atom to which they are attached;

$Y^-$ represents $Cl^\ominus$, $Br^\ominus$, $CH_3SO_3^\ominus$ or

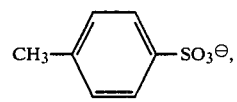

m represents an integer from 1 to 6; and p represents a number from 1 to 50.

2. The composition of claim 1 wherein $R_1$, $R_2$, $R_3$ and $R_4$ represent $CH_3$, m represents an integer from 1 to 4, p represents a number from 1 to 10 and A represents (1) —(CH$_2$)$_n$—wherein n represents an integer from 2 to 6, (2) —CH$_2$—CH=CH-CH$_2$—, (3) —CH$_2$—C≡C-CH$_2$—, (4) —CH—(CH$_2$)$_2$—,
      |
      CH$_3$ (5) —CH$_2$-CHOH-CH$_2$—, (6) —CH$_2$-CHOH-CH$_2$-O-CH$_2$-CHOH-CH$_2$—

(7) [CH$_2$-CH$_2$-O]$_x$-CH$_2$-CH$_2$—, wherein x is 1 to 15, (8) 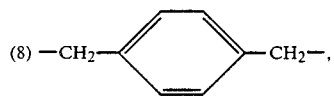

(9) 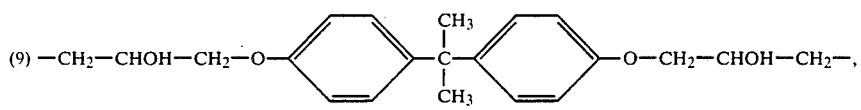

or

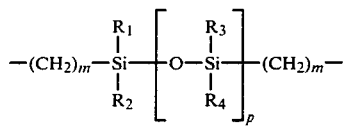

3. The composition of claim 1 wherein two adjacent $R_5$ radicals together with the $R_6$ radicals attached to the same nitrogen atoms, the said nitrogen atoms and the A radical therebetween form a triethylenediamino radical.

4. The composition of claim 1 wherein $R_6$ represents methyl, octyl or dodecyl or two $R_6$ radicals and A together with the nitrogen atoms connected thereto form a divalent piperazino ring.

5. The composition of claim 1 wherein $R_1$, $R_2$, $R_3$, $R_4$, $R_5$ and $R_6$ each represent $CH_3$, m=3, p=1, Y=Br and A=$(CH_2)_3$.

6. The composition of claim 1 wherein $R_1$, $R_2$, $R_3$, $R_4$, $R_5$ and $R_6$ each represent $CH_3$, m=3, p=3, Y=Cl and A=$(CH_2)_3$.

7. The composition of claim 1 wherein $R_1$, $R_2$, $R_3$, $R_4$, $R_5$ and $R_6$ each represent $CH_3$, m=1, p=1, Y=Br and A=$(CH_2)_3$.

8. The composition of claim 1 wherein $R_1$, $R_2$, $R_3$, $R_4$, $R_5$ and $R_6$ each represent $CH_3$, m=3, p=1, Y=Br and A=$(CH_2)_4$.

9. The composition of claim 1 wherein $R_1$, $R_2$, $R_3$, $R_4$ and $R_5$ each represent $CH_3$, $R_6$ represents $C_{12}H_{25}$, m=3, p=6, Y=BR and A=$(CH_2)_6$.

10. The composition of claim 1 wherein $R_1$, $R_2$, $R_3$, $R_4$ and $R_5$ each represent $CH_3$, $R_6$ represents $C_8H_{17}$, m=3, p=6, Y=Br and A=$CH_2$-CHOH-$CH_2$.

11. The composition of claim 1 wherein $R_1$, $R_2$, $R_3$ and $R_4$ each represent $CH_3$, the unit formed by $R_5$, $R_6$, A and the two nitrogens to which A is attached represent triethylenediamino radical of the formula

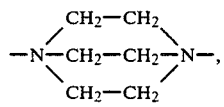

Y = Br, p = 6 and m = 3.

12. The composition of claim 1 wherein $R_1$, $R_2$, $R_3$, $R_4$ and $R_5$ each represent $CH_3$, $R_6$ and A together with the two nitrogen atoms to which A is attached form a piperazine ring, Y=Br, p=6 and m=3.

13. The composition of claim 1, in the form of a shampoo, which also contains an effective amount of at least one anionic, cationic, nonionic, amphoteric or zwitterionic surface-active agent.

14. The composition of claim 1, in the form of a hair dyeing composition, which also contains an effective amount of a hair dye.

15. The composition of claim 1 which also contains an effective amount of at least one anionic polymer.

16. A process for treating the hair, nails or skin which comprises applying thereto the composition of claim 1 in an amount sufficient to condition said hair, nails or skin.

17. A process for preparing a polyquaternary polysiloxane polymer having recurring units of the formula

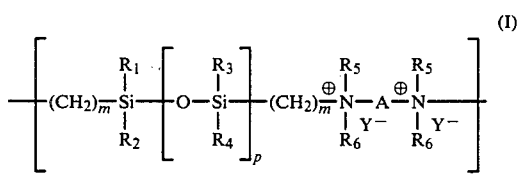 (I)

wherein

A represents a divalent α,ω-bis-(alkyl)-polysiloxane group or a linear or branched, saturated or unsaturated hydrocarbon chain containing up to 6 consecutive carbon atoms, optionally substituted by one or more hydroxyl groups and optionally substituted by one or more chain oxygen atoms and/or aromatic rings;

$R_1$, $R_2$, $R_3$ and $R_4$ each independently represent a $C_1$-$C_6$ alkyl radical or a phenyl radical;

$R_5$ represents methyl, ethyl or hydroxyethyl;

$R_6$ represents a $C_1$-$C_{18}$ alkyl radical or two adjacent $R_6$ radicals together with the nitrogen atom to which they are attached and the A radical therebetween form a divalent piperazino radical;

or two adjacent $R_5$ radicals together with the two adjacent $R_6$ radicals attached to the same nitrogen atoms, the said nitrogen atoms and the A radical therebetween form a triethylenediamino radical, or $R_5$ and $R_6$ together represent a heterocycle with the nitrogen atom to which they are attached;

$Y^-$ represents $Cl^\ominus$, $Br^\ominus$, $CH_3SO_3^\ominus$ or

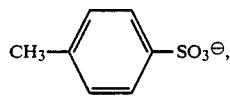

m represents an integer from 1 to 6; and p represents a number from 1 to 50, said process comprising reacting in a solvent at a temperature of 80° to 150° C. a siloxane having the formula:

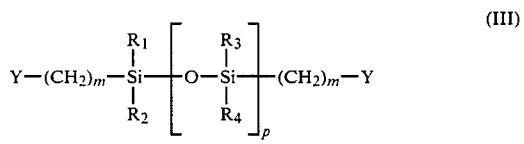 (III)

wherein $R_1$, $R_2$, $R_3$, $R_4$, Y, p and m have the meanings given above, with a bis-tertiarydiamine of the formula

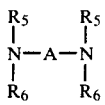   (IV)

wherein $R_5$, $R_6$ and A have the meanings given above.

18. The process of claim 17 wherein the bis-tertiarydiamine of formula IV is
N,N'-tetramethylethylenediamine,
N,N'-tetramethylpropylenediamine,
N,N'-tetramethylbutylenediamine,
N,N'-tetramethylhexamethylenediamine,
N,N'-dimethyl-N,N'-dialkyl($C_1$–$C_{18}$)-alkylene ($C_2$–$C_6$) diamine,
1,4-tetramethyldiaminobut-2-ene,
1,4-tetramethyldiaminobut-2-yne,
dihydroxyethylpiperazine,
1,3-bis-(methyl-alkyl($C_1$–$C_{18}$)amino)-propan-2-ol,
1,3-bis-(methylhydroxyethylamino or ethylhydroxyethylamino)propan-2-ol, or
1,3-bis-(morpholino)-propan-2-ol.

19. The process of claim 17 wherein the siloxane of formula III is prepared by reacting a dialkylchlorosilane, a diphenylchlorosilane, an alkylphenylchlorosilane or a mixture thereof with an allyl halide in the presence of a platinum or chloroplatinic acid catalyst and hydrolyzing and condensing the resulting compound so as to produce bis-halogenopropyl-1,1,3,3-tetraalkyldisiloxane, bis-halogenopropyl-1,1,3,3-tetraphenyldisiloxane or a mixture thereof.

20. The process of claim 17 wherein the siloxane of formula III is prepared by reacting dialkylchlorosilane, diphenylchlorosilane or a mixture thereof with allyl acetate in the presence of a platinum or chloroplatinic acid catalyst so as to produce as product (a), acetoxypropyl-dialkylchlorosilane, acetoxypropyl-diphenylchlorosilane or a mixture thereof, hydrolyzing said product (a) so as to produce as product (b) 1,3-bis-(3-hydroxypropyl)-1,1,3,3-tetraalkyldisiloxane, 1,3-bis-(3-hydroxypropyl)-1,1,3,3-tetraphenyldisiloxane or a mixture thereof, and halogenating product (b) so as to produce 1,3-bis-(halogenopropyl)-1,1,3,3-tetraalkyldisiloxane, 1,3-bis-(halogenopropyl)-1,1,3,3-tetraphenyldisiloxane or a mixture thereof.

21. The process of claim 17 wherein the siloxane of formula III is prepared by reacting a dialkyldichlorosilane, a diphenyldichlorosilane, an alkylphenyldichlorosilane or a mixture thereof with a
(1) dialkyl-halogenoalkyl-halogenosilane,
(2) dialkyl-acetoxyalkyl-halogenosilane,
(3) dialkyl-acetoxyalkyl-acetoxysilane,
(4) tetraalkyl-acetoxyalkyl-acetoxydisiloxane,
(5) dialkyl-halogenoalkyl-methoxysilane,
(6) dialkyl-halogenoalkyl-ethoxysilane,
(7) dialkyl-acetoxyalkyl-methoxysilane
(8) dialkyl-acetoxyalkyl-ethoxysilane,
(9) tetraalkyl-halogenoalkyl-methoxydisiloxane,
(10) tetraalkyl-halogenoalkyl-ethoxydisiloxane,
(11) tetraalkyl-acetoxyalkyl-methoxydisiloxane or
(12) tetraalkyl-acetoxyalkyl-ethoxydisiloxane.

22. A process for preparing a polyquaternary polysiloxane polymer having recurring units of the formula

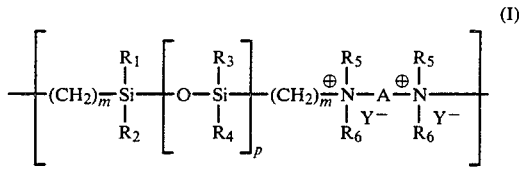   (I)

wherein
A represents a divalent α,ω-bis-(alkyl)-polysiloxane group or a linear or branched, saturated or unsaturated hydrocarbon chain containing up to 6 consecutive carbon atoms, optionally substituted by one or more hydroxyl groups and optionally substituted by one or more chain oxygen atoms and/or aromatic rings;
$R_1$, $R_2$, $R_3$ and $R_4$ each independently represent a $C_1$–$C_6$ alkyl radical or a phenyl radical;
$R_5$ represents methyl, ethyl or hydroxyethyl;
$R_6$ represents a $C_1$–$C_{18}$ alkyl radical or two adjacent $R_6$ radicals together with the nitrogen atom to which they are attached and the A radical therebetween form a divalent piperazino radical;
or two adjacent $R_5$ radicals together with the two adjacent $R_6$ radicals attached to the same nitrogen atoms, the said nitrogen atoms and the A radical therebetween form a triethylenediamino radical, or $R_5$ and $R_6$ together represent a heterocycle with the nitrogen atom to which they are attached;
$Y^-$ represents $Cl^\ominus$, $Br^\ominus$, $CH_3SO_3^\ominus$ or

m represents an integer from 1 to 6; and
p represents a number from 1 to 50,
said process comprising reacting at a temperature of 80° to 150° C. bistertiarydiamine of the formula:

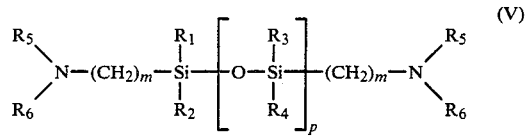   (V)

with a bis-halogenated, bis-mesylated or bis-tosylated derivative of the formula, Y-A-Y (VI), wherein $R_1$, $R_2$, $R_3$, $R_4$, $R_5$, $R_6$, m, p, Y and A have the meanings given above, in water, a lower alcohol, glycol, glycol ether, aliphatic hydrocarbon, aromatic hydrocarbon, ketone or a mixture thereof, optionally under pressure.

* * * * *